United States Patent
Goldstein et al.

(10) Patent No.: US 8,551,462 B2
(45) Date of Patent: Oct. 8, 2013

(54) COSMETIC COMPOSITION AND METHOD FOR RETARDING HAIR GROWTH

(75) Inventors: Mindy S. Goldstein, Plainview, NY (US); Chia Wen Chen, New Rochelle, NY (US); Christina G. Fthenakis, Dix Hills, NY (US); Kenneth D. Marenus, Dix Hills, NY (US); Thomas Mammone, Farmingdale, NY (US)

(73) Assignee: ELC Management, LLC, New York, NY (US)

(*) Notice: Subject to any disclaimer, the term of this patent is extended or adjusted under 35 U.S.C. 154(b) by 42 days.

(21) Appl. No.: 12/786,684

(22) Filed: May 25, 2010

(65) Prior Publication Data

US 2011/0104251 A1    May 5, 2011

Related U.S. Application Data

(62) Division of application No. 11/031,172, filed on Jan. 7, 2005, now abandoned.

(60) Provisional application No. 60/535,125, filed on Jan. 7, 2004.

(51) Int. Cl.
*A61K 8/00* (2006.01)

(52) U.S. Cl.
USPC .................................................. 424/70.1

(58) Field of Classification Search
None
See application file for complete search history.

(56) References Cited

U.S. PATENT DOCUMENTS

| | | | |
|---|---|---|---|
| 4,499,072 A | 2/1985 | Sunkara et al. | |
| 4,720,489 A | 1/1988 | Shander | |
| 4,745,104 A | 5/1988 | Jacobs et al. | |
| 4,849,410 A | 7/1989 | Jacobs et al. | |
| 5,565,207 A | 10/1996 | Kashibuchi et al. | |
| 5,804,168 A * | 9/1998 | Murad | 424/59 |
| 6,025,334 A * | 2/2000 | Dupont et al. | 424/729 |
| 6,093,748 A | 7/2000 | Ahluwalia et al. | |
| 6,124,364 A * | 9/2000 | Breton et al. | 514/733 |
| 6,153,208 A | 11/2000 | McAtee et al. | |
| 6,235,737 B1 | 5/2001 | Styczynski et al. | |
| 6,375,948 B1 | 4/2002 | Tsuji et al. | |
| 6,391,850 B2 | 5/2002 | Bouck et al. | |
| 6,403,618 B1 | 6/2002 | Fernandez-Pol | |
| 6,407,056 B1 | 6/2002 | Seiberg et al. | |
| 6,440,434 B1 | 8/2002 | Barrett et al. | |
| 6,451,777 B1 | 9/2002 | Bradbury et al. | |
| 6,482,857 B1 * | 11/2002 | Bradbury et al. | 514/557 |
| 6,608,107 B2 | 8/2003 | Wong et al. | |
| 6,680,062 B2 * | 1/2004 | Muizzuddin et al. | 424/401 |
| 6,919,088 B2 | 7/2005 | Hebert | |
| 6,982,284 B1 * | 1/2006 | Brown et al. | 514/577 |
| 2003/0039668 A1 | 2/2003 | Gulla et al. | |

FOREIGN PATENT DOCUMENTS

| | | |
|---|---|---|
| EP | 0 943 311 | 9/1999 |
| EP | 1 352 637 | 10/2003 |
| JP | 07-238037 | 9/1995 |
| JP | 11-511448 | 10/1999 |
| JP | 11-322548 | 11/1999 |
| JP | 2000-344614 | 12/2000 |
| JP | 2002-308729 | 10/2002 |
| JP | 2003-261454 | 9/2003 |
| WO | WO 85/02543 | 6/1985 |
| WO | WO 86/02269 | 4/1986 |
| WO | WO 94/21217 | 9/1994 |
| WO | WO95/04526 | 2/1995 |
| WO | WO 96/09806 | 4/1996 |
| WO | WO 97/19672 | 6/1997 |
| WO | WO 97/19673 | 6/1997 |
| WO | WO 00/33846 | 6/2000 |
| WO | WO 02/07697 | 1/2002 |
| WO | WO 03/015729 | 2/2003 |

OTHER PUBLICATIONS

Shin, et al., The Junceellolides, New Anti-Inflammatory Diterpenoids of the Briarane Class from the Chinese Gorgonian Junceella fragilis; Tetrahedron; vol. 45; No. 6; pp. 1633-1638; Printed in Great Britian; 1989.
Look, et al.; The pseudopterosins: Anit-inflammatory and analgesic natural products from the sea whip Pseudopterogorgia elisabethae; Proc. Natl. Acad. Sci.; vol. 83; pp. 6238-6240; USA; Sep. 1986.
Balsam and Sagarin; Cosmetics Science and Technology; 2nd Edition; vol. 2; pp. 443-465; Mar. 1972.
PCT International Search Report; International Application No. PCT/US05/00383; Completion Date: Sep. 5, 2006; Date of Mailing: Sep. 26, 2006.
PCT Written Opinion of the International Searching Authority, Or The Declaration; International Application No. PCT/US05/00383; Completion Date: Sep. 5, 2006; Date of Mailing: Sep. 26, 2006.

* cited by examiner

*Primary Examiner* — Anand Desai
*Assistant Examiner* — Melissa Mercier
(74) *Attorney, Agent, or Firm* — Idris N. McKelvey (57) ABSTRACT

The present invention comprises cosmetic compositions and methods for retarding hair growth comprising a combination of an ornithine decarboxylase inhibitor, an anti-angiogenic active and an anti-inflammatory.

15 Claims, 4 Drawing Sheets

Figure 1. Beard Growth Retardant Product Results of Beard Self Assessment

*Figure 2. Beard Growth Retardant Product
Results of product evaluation after 8 weeks of use*

Figure 3. Evaluation of Beard Growth Retardant Product Results from Digital Images via Image Analysis

*Figure 4. Hair Growth Retardation Complex vs.
A conventional hair growth retardation product
% Reduction in Hair Growth*

COSMETIC COMPOSITION AND METHOD FOR RETARDING HAIR GROWTH

This application is a divisional of U.S. patent application Ser. No. 11/031,172, filed Jan. 7, 2005, now abandoned which in turn claims priority from U.S. provisional application 60/535,125 filed Jan. 7, 2004.

FIELD OF THE INVENTION

The present invention relates to skin care cosmetic compositions and methods. In particular, the present invention relates to novel cosmetic compositions and methods for retarding hair growth.

BACKGROUND OF THE INVENTION

For years, companies have marketed products for either hair growth or hair growth retardation, with limited success. From mechanical procedures to compositions containing biologically active ingredients, numerous means are available for the consumer. Use of hair dyes to color hair, require frequent repetitions and are not often effective in hiding the appearance of hair on the skin.

Especially in suppressing hair growth, the prior art has taught the use of numerous actives including biological enzymes, plant extracts and enzyme inhibitors. For example, U.S. Pat. No. 6,375,948 teaches the use of an extract of a plant of the family *Juniperus* or a malt, an elastase inhibitor or neutral endopeptidase inhibitor and a proteolytic enzyme to suppress hair growth. In U.S. Pat. No. 6,407,056, the patent teaches a method of delaying mammalian hair growth comprising topically applying an effective amount of a composition comprising a serine protease and a pharmaceutically or cosmetically acceptable vehicle.

The references discussed above have limited and only short term usefulness. Other references turn to the factors that are believed to contribute to hair growth to develop formulas for regulating hair growth.

For example, angiogenesis is the fundamental process by which new blood vessels are formed. The process involves the migration of vascular endothelial cells into tissue, followed by the condensation of such endothelial cells into vessels. Angiogenesis involves a complex interplay of molecules that stimulate and molecules that inhibit the growth and migration of endothelial cells. In U.S. Pat. No. 6,391,850, it was found that an anti-angiogenic, SLED, stimulated the growth of hair. It was believed that SLED affected hair growth by mediating angiogenesis within the hair follicle.

Sphingo Glycolipids, such as phytosphingosine (known to be an anti-angiogenic), have been used in skin care compositions to aid in hair growth. For example, U.S. Pat. No. 5,565,207 ("Patent '207") teaches the use of a scalp moisturizer comprising a steroid glycoside and/or a triterpenoid glycoside, a sphingo glycolipid and a follicular hormone and/or an adrenocortical hormone. Patent '207 recognizes the use of the scalp moisturizer to stimulate hair growth.

It is important to note that the references discussed above teach the use of anti-angiogenics to aid in promoting hair growth.

Yet another factor believed to contribute to hair growth is Ornithine Decarboxylase (OCD), an enzyme that catalyzes the decarboxylation of ornithine to putrescine. The reaction is the first step in the biosynthesis of the polyamides known as spermidine and spermine. The polyamides are known to play an important role in cell growth and proliferation. U.S. Pat. No. 4,720,489 ("Patent '489") teaches the use of ornithine decarboxylase inhibitors to retard hair growth. Patent '489 specifically teaches against the use of certain ornithine decarboxylase inhibitors that can have secondary pharmacological effects.

In summary, the references discussed above teach that anti-angiogenic agents promote hair growth while certain ornithine decarboxylase inhibitors retard hair growth. Still other references teach compositions with only limited efficacy.

There still remains a need for a novel composition and method for inhibiting hair growth that has prolonged efficacy that can be accomplished preferably by manipulating the numerous factors that contribute to hair growth.

SUMMARY OF THE INVENTION

The present invention comprises a cosmetic composition comprising from 0.1 to 50% of an ornithine decarboxylase inhibitor, from 0.01 to 10% of an anti-angiogenic active, from 0.0001 to 20% of an anti-inflammatory and a cosmetically acceptable vehicle.

The present invention further comprises a method of retarding hair growth comprising applying a composition comprising from 0.1 to 50% of an ornithine decarboxylase inhibitor, from 0.01 to 10% of an anti-angiogenic active, from 0.0001 to 20% of an anti-inflammatory and a cosmetically acceptable vehicle.

DETAILED DESCRIPTION

Except in operating and comparative examples, or where otherwise explicitly indicated, all numbers in this description indicating amounts or ratios of material or conditions of reaction, physical properties of materials and/or use are to be understood as modified by the word "about." All amounts are by weight of the final composition, unless otherwise specified.

It has been surprisingly discovered that the combination of an ornithine decarboxylase inhibitor with an anti-angiogenic active and an anti-inflammatory effectively suppresses hair growth.

In a preferred embodiment, the ornithine decarboxylase inhibitor is derived from a marine, synthetic, or naturally derived source as opposed to an animal derived source. Preferred inhibitors are pentacyclic triterpenes. Examples of pentacyclic triterpenes include ursolic acid, betulin, betulinic acid, oleanolic acid, betulin mono and di-succinate or glutarate. Particularly preferred is ursolic acid extracted from *Rosmarinus officinalis*, which is commercially available from Sabinsa Corporation in 121 Ethel Road West, Unit #6, Piscataway, N.J. 08854.

The amount will vary depending on the formulation and the performance desired. The ornithine decarboxylase inhibitor is used in an amount from 0.001% to 90% by weight of the composition is used. Preferably, an amount of from 0.001% to 60% is used and most preferably, an amount of from 0.01% to 3% is used.

The preferred composition further comprises an anti-angiogenic active. Although anti-angiogenic agents have been known to promote hair growth, it has been surprisingly found that an anti-angiogenic can aid in the inhibition of hair growth in the present inventive combination. Particularly preferred anti-angiogenics include sphingo lipids. Examples of sphingo lipids include phytosphingosine, dihydrosphingosine, sphingosine, dehydrophytosphingosine, monohexosylceramide, sphingoplamalogen, acetyl sphingosine and monohexaosylceramide fatty acid ester. Other anti-angiogenic agents include magnolia extract, MDI complex (shark cartilage) and tetrahydrocurcumin and extracts of green tea.

The amount will vary depending on the formulation and the performance desired. In general, the anti-angiogenic is used in an amount from 0.001% to 90% by weight of the composition is used. Preferably, an amount of from 0.01% to 60% and most preferably, an amount of from 0.1% to 2% is used.

Inflammation and related irritation can detrimentally interfere with the ability of actives to penetrate the skin and provide their intended benefit. Anti-inflammatories have been used in hair growth compositions to enhance the activity of hair growth promoting actives (See U.S. Pat. No. 6,451,777). However, in the present invention, it has been surprisingly discovered that an anti-inflammatory when combined with an ornithine decarboxylase inhibitor and an anti-angiogenic agent actually aids in inhibiting hair growth.

The anti-inflammatory used in the present invention can be selected from any known in the art. A particularly preferred anti-inflammatory is gorgonian extract. Gorgonian extract is a marine-derived, natural extract available from the Lipo Chemical Company, Patterson, N.J. as a liquid extract of Sea Whip, pseudopterogorgia elisabethae, supplied as a 4% Sea Whip extract in butylene glycol. The Caribbean Sea Whip pseudoptemgorgia elisabethae has been reported in Proc. Natl. Acad. Sci. USA, Vol. 83, pp. 6238-6240 (September 1986) as containing pseudopterosins which are diterpene-pentose glycosides. U.S. Pat. No. 4,849,410 and U.S. Pat. No. 4,745,104, incorporated by reference herein, provide further disclosure on the Caribbean gorgonians. Alternatively, anti-inflammatories such as boswellin, hoelen extract, ximenynic acid, hesperitin, tea polyphenols and licorice extract may be used.

The amount will vary depending on the formulation and the performance desired. Specifically, amounts of an anti-inflammatory such as gorgonian extract for purposes of this invention will range from 0.00001% to 20%, preferably from 0.0001% to 5%, and most preferably from 0.1% to 1% by weight.

It has been surprisingly found that hair growth can be significantly inhibited by addition of a 5 alpha reductase inhibitor to the inventive combination. It is known that 5 alpha reductase promotes the formation of 5 dihydrotestosterone (DHT), a product of testosterone. DHT is the hormone in skin that stimulates hirsutism, which is male pattern hair growth. It is believed that reducing DHT can result in reduction of hirsutism or male pattern hair loss. Therefore, inhibiting the formation of 5 alpha reductase is believed to prevent the formation of DHT and therefore prevent hirsutism and prevent male pattern hair loss. Surprisingly, however, it is believed that combining a 5 alpha reductase inhibitor with the presenting inventive composition helps retard hair growth in all areas of the body, including areas with typical male pattern hair loss, as shown in Example 3 below.

Suitable 5 alpha reductase inhibitors include inhibitors commonly known in the art and include but are not limited to saw palmetto, woodworm (Artemisinin), liposome encapsulated azuleic acid (Azelosome), clove extract (Chouji Liquid), Zinc salt of L-Pyrrolidone Carboxylic Acid (Zincidone®), mixture of water, hydrolyzed soy protein, 3-aminopropane, sulfonic acid and sodium chondroitin sulfate (Capigen), seaweed extract (Phlorogine), isolutrol, progesterone, (5, 20-R)-4-diazo-21-hydroxy-20-methyl pregnan-3-one, (4R)-5-10-seco-19-Norpregna-4,5-diene-3,10,20 trione, 4-androstene-3-one-17-carboxylic acid, and its methyl ester, 17-beta-N,N-diethylcarbamoyl-9-methyl-4-aza-5-alpha-androstane-3-one, 11-alpha-OH-progesterone, 17-alpha-OH-progesterone, and 20-alpha-OH-progesterone.

The amount will vary depending on the formulation and the performance desired. Preferably, the 5 alpha reductase inhibitor is saw palmetto and is present in the amount from 0.0001% to 10%, more preferably from 0.001% to 5% and most preferable from 0.01% to 1%.

In yet another alternate preferred embodiment, the appearance of hair can be further reduced by the addition of a whitening agent in the inventive formulations. Suitable whitening agents include yeast extract (Yeast AE), ferulic acid, BV-OSC (vitamin C derivative from Barnet), Na+ hinokitiol, licorice extract (glabridin), etioline (extract of mitracarpus & bearberry in combination with glycerin and butylene glycol), phytoclar II (mulberry & *scutellaria* from Coletica), arbutin, resveratrol and kojic acid. Particularly preferred is glabridin obtained from Alchem Internationl Ltd., at 201, Empire Plaza, Mehrauli-Gurgaon Road, Sultanpur, New Delhi, India.

The amount will vary depending on the formulation and the performance desired. Preferably, the whitening agent is present in the amount from 0.0001% to 20%, more preferably from 0.001% to 15% and most preferable from 0.01% to 10%.

It is believed that a component with estrogen-like activity may surprisingly aid in compositions for the retardation of hair growth. Therefore, in an alternate preferred embodiment, the present invention further comprises an estrogen-like component. Particularly preferred supplements are plant extracts such as solgen-40 C (a soy extract), wild yam and ginseng or phytoestrogens derived therefrom. Particularly preferred is solgen-40 C obtained from Solbar Hatzor Ltd. located in Kibbutz Hatzor, P.O. Box 2230, Ashdod, Israel, 77121.

The amount will vary depending on the formulation and the performance desired. Preferably, the plant extract is present in an amount of 0.0001% to 25%, more preferably from 0.001% to 15% and most preferably from 0.01% to 10%.

In yet another preferred embodiment, the present inventive composition may contain conventional hair removal ingredients (such as thioglycollate) in any amount desired as would be compatible with the present composition. A list of conventional hair removal ingredients can be found in the International Cosmetic Ingredient Dictionary, CTFA, Sixth Edition, 1995.

The composition further comprises a cosmetically acceptable vehicle that is suitable for topical application to skin, hair and/or nails. Cosmetically acceptable vehicles are well known in the art and are selected based on the end use of the application. For example, vehicles of the present invention include, but are not limited to, those suitable for application to the skin. Such vehicles are well known to those of ordinary skill in the art, and can include one or more compatible liquid or solid filler diluents or vehicles which are suitable for application to the skin. The exact amount of vehicle will depend upon the level of any other optional ingredients that one of ordinary skill in the art would classify as distinct from the vehicle (e.g., other active components). The compositions of the present invention preferably comprise from about 40% to about 99.99%, more preferably from about 70% to about 99.99%, and most preferably from about 80% to about 98%, by weight of the composition, of a vehicle.

The vehicle and the compositions herein can be formulated in a number of ways, including but not limited to emulsions. For example, suitable emulsions include oil-in-water, water-in-oil, water-in-oil-in-water, oil-in-water-in-oil, and oil-in-water-in-silicone emulsions. Preferred compositions comprise an oil-in-water emulsion.

The compositions of the present invention can be formulated into a wide variety of product types, including shampoos, creams, waxes, pastes, lotions, milks, mousses, gels, oils, tonics and sprays. Preferred compositions are formulated into lotions, creams, gels, shampoos and sprays. These product forms may be used for a number of applications, including but not limited to, hand and body lotions, cold creams, facial moisturizers, anti-acne preparations, topical analgesics, make-ups/cosmetics including foundations, eye-shadows, lipsticks and the like. Any additional components required to formulate such products vary with product type and can be routinely chosen by one skilled in the art.

If compositions of the present invention are formulated as an aerosol and applied to the skin as a spray-on product, a propellant is added to the composition. Examples of suitable propellants include chlorofluorinated lower molecular weight hydrocarbons. A more complete disclosure of propellants useful herein can be found in Sagarin, Cosmetics Science and Technology, 2nd Edition, Vol. 2, pp. 443-465 (1972).

Other Components

The formulation also can comprise other components that may be chosen depending on the carrier and/or the intended use of the formulation. Additional components include, but are not limited to, water soluble sunscreens (such as Eusolex 232); oil soluble sunscreens (such as octyl methoxycinnamate); and organic sunscreens (such as camphor derivatives, cinnamates, salicylates, benzophenones, triazines, PABA derivatives, diphenylacrylate derivatives, and dibenzoylmethane derivatives.); antioxidants (such as BHT); chelating agents (such as disodium EDTA); emulsion stabilizers (such as carbomer); preservatives (such as methyl paraben); fragrances (such as pinene); flavoring agents (such as sorbitol); humectants (such as glycerine); waterproofing agents (such as PVP/Eicosene copolymer); water soluble film-formers (such as hydroxypropyl methylcellulose); oil-soluble film formers (such as hydrogenated C-9 Resin); moisturizing agents, such as cholesterol; cationic polymers (such as Polyquatenium 10); anionic polymers (such as xanthan gum); vitamins (such as tocopherol); and the like.

The compositions can also encompass one or more active components, and as such can be either cosmetic or pharmaceutical compositions. Examples of useful actives include, but are not limited to, those that improve or eradicate age spots, keratoses and wrinkles, analgesics, anesthetics, anti-acne agents, antibacterials, antiyeast agents, antifungal agents, antiviral agents, antidandruff agents, antidermatitis agents, antipruritic agents, antiemetics, antihyperkeratolytic agents, anti-dry skin agents, antiperspirants, antipsoriatic agents, antiseborrheic agents, hair conditioners and hair treatment agents, antiaging agents, antiwrinkle agents, antiasthmatic agents and bronchodilators, sunscreen agents, antihistamine agents, depigmenting agents, wound-healing agents, vitamins, corticosteroids, tanning agents or hormones. More specific examples of useful active agents include retinoids such as retinol, and esters, acids, and aldehydes thereof; ascorbic acid, and esters and metal salts thereof, tocopherol and esters and amide derivatives thereof; shark cartilage; milk proteins; alpha- or beta-hydroxy acids; DHEA and derivatives thereof; topical cardiovascular agents; clotrimazole, ketoconazole, miconozole, griseofulvin, hydroxyzine, diphenhydramine, pramoxine, lidocaine, procaine, mepivacaine, monobenzone, erythromycin, tetracycline, clindamycin, meclocyline, hydroquinone, minocycline, naproxen, ibuprofen, theophylline, cromolyn, albuterol, hydrocortisone, hydrocortisone 21-acetate, hydrocortisone 17-valerate, hydrocortisone 17-butyrate, betamethasone valerate, betamethasone diproprionate, triaminolone acetonide, fluocinonide, clobetasol, proprionate, benzoyl peroxide, crotamiton, propranol, promethazine, and mixtures thereof.

Particularly preferred embodiments of the present formulations are moisturizing after-shaves. To that end, the present formulations are combined with agents that are moisturizers, emollients or humectants. Examples of useful combinations are oils, fats, waxes, esters, fatty acid alcohols, fatty acid ethoxylates, glycols, sugars, hyaluronic acid and hyaluronates, dimethicone, cyclomethicone, and the like. Further examples can be found in the International Cosmetic Ingredient Dictionary, CTFA, Sixth Edition, 1995.

Method of Retardation of Hair Growth

The present inventive compositions are particularly useful as hair growth retardation products. The present inventive compositions and methods of the present invention provide a unique combination that surprisingly retards hair growth. Hair growth can be retarded on the face including eyebrows, upper lips, and sideburns, on the body including legs, ears and back, and any other area of the body where undesired hair growth may occur. The present inventive compositions are particularly preferred to prevent hair growth after shaving.

The present inventive method comprises administering or topically applying to the skin a safe and effective amount of the combination of the present invention. The amounts of the components in the compositions will vary widely depending upon the level of hair growth already in existence in the subject (if such exists), the rate of further hair growth, and the level of regulation desired.

A preferred amount of cosmetically or pharmaceutically treating the skin is via chronic topical application of a safe and effective amount of the novel composition to regulate hair growth. The amount of the composition and the frequency of topical application to the skin can vary widely, depending upon the rate of hair growth for the individual. It is well within the purview of the skilled artisan, such as a dermatologist or other health care provider, to regulate pharmaceutical dosages according to patient needs. The method of the present invention is particularly useful after shaving.

It is suggested as an example that topical application range from about once per week to about 4 or 5 times daily, preferably from about 3 times a week to about 3 times daily, most preferably about once or twice per day. In a preferred embodiment, the present method is utilized as an aftershave and can be applied directly to the face after shaving. The compositions will comprise from about 0.001% to 5%, preferably from about 1% to 5%, and most preferably from about 1% to 4% of the active components.

The following examples further illustrate the invention, but the invention is not limited thereto.

EXAMPLE 1

Clinical Study

A composition comprising the preferred embodiment was applied on the face of male volunteers and evaluated for its ability to make beard hair less noticeable by retarding hair growth, lightening facial hair or reducing the appearance of 5 o'clock shadow.

Study Design:

1. Subject Selection/Inclusion Criteria:

Fourteen men with normal to heavy and dark facial (beard) hair, who are in good general health and free of any dermatological disorders, were qualified for this study.

2. Clinical Protocol:

At every visit the men arrive at the lab between 7-8 am without shaving. They bring their razor with a new blade and regular shave product and shave at the lab. Immediately after shaving, closeness of shave is documented by taking close-up photographs with the digital camera. The subjects return to the lab after 8 hours and 24 hours and are photographed again to document 5 o'clock shadow and 24 hour beard hair growth.

At the end of the first visit the subjects are given a product containing the inventive composition of the present invention (hereinafter "Product"), which they use 2 times a day for 4 weeks. For the duration of this study the subjects are asked to use the same shave product every time they shave. They are instructed not to use the product on the day of testing. The subjects are given a very brief questionnaire at every 8 and 24 hour time point to evaluate beard texture, color, and appearance. At the end of the study they are given more a comprehensive questionnaire to evaluate the product. At Weeks 1, 2, 4 and 8 the subjects return for testing and the above procedures are repeated every time.

3. Composition:

| | | |
|---|---|---|
| Ceteareth-12 | Eumulgin B-1 | 3.2% |
| PEG-10 Soya Sterol | Generol 122 | 1.0% |
| Sorbitan Sesquioleate | Arlacel 83V | 0.1% |
| Glyceryl Stearate SE | Glyceryl Monostearate 24 SE | 2.6% |
| Coco-Caprylate/Caprate | Cetiol LC | 3.0% |
| Stearic Acid | Dermofat 4919 | 0.1% |
| Stearyl Alcohol/Ceteareth-20 | Promulgen G-CG | 0.5% |
| Hydrogenated Lecithin | Lecinol S-10 | 0.1% |
| Cholesterol | NAB Cholesterol | 0.2% |
| Glycereth-26 | Liponic EG1 | 0.2% |
| Octyldodecanol | Eutanol G NF | 0.1% |
| Phytoshingosine | DS-Phytosphingosine | 0.1% |
| Purified Water | Deionized Water | 68.546% |
| Disodium EDTA | Disodium EDTA/Trilon BD | 0.1% |
| Phenoxyethanol/Chlorphenesin/Glycerin/Methyl Paraben/Benzoic Acid | Germazide MPB | 1.0% |
| Potassium Sorbate | Sorbistat K | 0.1% |
| Methylparaben | Methyl Paraben NF | 0.35% |
| Pemulen TR-1 (2% disp in MethylP) | Deionized water 4.8925%, Acrylates/C10-30 Alkyl Acrylate Crosspolymer 0.1%, Methyl Paraben NF 0.0075% | 5.0% |
| Purified Water (97.85%) | Deionized Water | 4.0% |
| Polyquaternium-10 (2%) | Polymer LR-400 (UCARE) | 0.004% |
| Butylene Glycol (0.15%) | 1,3 Butylene Glycol | 5.0% |
| *Glycyrrhiza Glabra* (Licorice) Extract | Glabridin | 0.05% |
| Ursolic Acid | Ursolic Acid 90% | 0.2% |
| Cyclomethicone | Dow Corning 245 Fluid | 2.0% |
| Hyaluronic Acid (1% SOL) | | 0.5% |
| Purified Water (98.10%) | Deionized Water | 0.4905% |
| Sodium Hyaluronate (1%) | Sodium Hyaluronate HMW | 0.005% |
| Phenoxyethanol (.70%) | Emeressence 1160 (Rose Ether) | 0.0035% |
| Yeast Extract | Yeast Extract AE | 1.0% |
| Soy Isoflavones | Solgen 40 | 0.2% |
| Butylene Glycol | | |
| Sea Whip Extract | Gorgonian Extract BG/NP | 0.5% |
| Phenoxyethanol | Emeressence 1160 (Rose Ether) | 0.25% |

Figure 1:
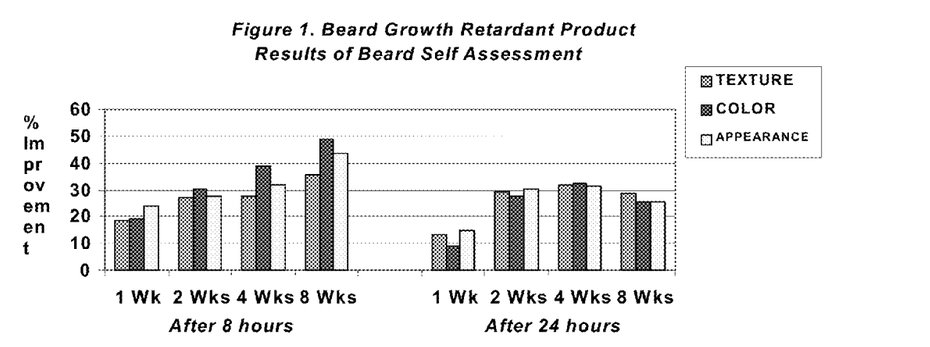
FIG. 1. Chart depicting results of Self Assessment of product containing inventive composition of the present invention from the Clinical Study in Example 1.
Figure 2:
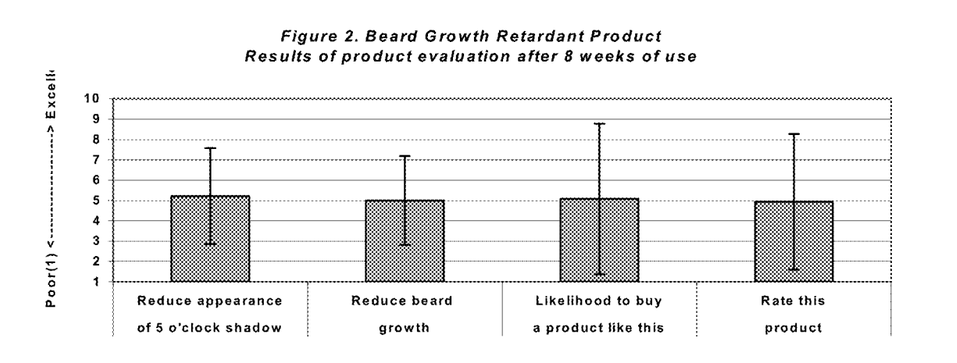
FIG. 2. Chart depicting results of product evaluation after eight weeks of use from the Clinical Study in Example 1.

Data Analysis:

Self-assessment and product evaluation questionnaires are compiled and the average results are shown on Tables 1-2 and FIGS. 1-2. Beard growth is evaluated from the digital photographs via image analysis. A template of the right and left side of the face of each subject is made and the amount of beard hair within this area is measured at each time point. The amount of hair covering the outlined area is directly related to hair length and therefore to hair growth.

Results:

The results of this study show that topical treatment with a product containing the above composition is effective in improving beard texture, color and appearance and reducing beard growth. Table 1 below and FIG. 1 summarize the results of the study.

TABLE 1

Self Assessment of Beard
% Improvement of Texture, Color and Appearance

| | 8 hours after shaving | | | | 24 hours after shaving | | | |
|---|---|---|---|---|---|---|---|---|
| | 1 Wk | 2 Wks | 4 Wks | 8 Wks | 1 Wk | 2 Wks | 4 Wks | 8 Wks |
| TEXTURE | 18.8 | 27.1 | 27.8 | 35.4 | 13.5 | 29.1 | 32.1 | 28.7 |
| COLOR | 19.4 | 30.1 | 38.6 | 49.0 | 9.1 | 27.5 | 32.5 | 25.6 |
| APPEARANCE | 23.8 | 27.4 | 32.1 | 43.6 | 15.0 | 30.2 | 31.3 | 25.6 |

As seen from Table 1 above and corresponding FIG. 1, self-assessment of beard texture, color and appearance at 8 and 24 hours after shaving clearly show an improvement with product use. After 1 week of treatment there was about a 20% improvement in texture, color and appearance of 5 o'clock shadow (8 hours after shaving) and it increased to about 35-50% after 8 weeks of treatment. At the 24 hour time point there was a 10-15% improvement after 1 week of treatment and increased to 25-30% between 2 and 8 weeks of treatment.

User's assessment of product's performance after 8 weeks of use are shown below. The users were asked to comment on the reduction of 5 o'clock shadow, beard growth, rate the product and likelihood to purchase it. Table 2 below and corresponding FIG. 2 summarize these results.

TABLE 2

Evaluation of Beard Growth Retardant Product after 8 Weeks of use
Results based on a scale from 1 (Poor)-10 (Excellent)

| Comment | Average Score | S.D. |
|---|---|---|
| Reduce appearance of 5 o'clock shadow | 5.2 | 2.4 |
| Reduce beard growth | 5.0 | 2.2 |
| Likelihood to buy a product like this | 5.1 | 3.7 |
| Rate this product | 4.9 | 3.3 |

As seen in Table 2 above and FIG. 2, on a scale of poor (1) to excellent (10) the participants rated the composition about a 5.

Figure 3:
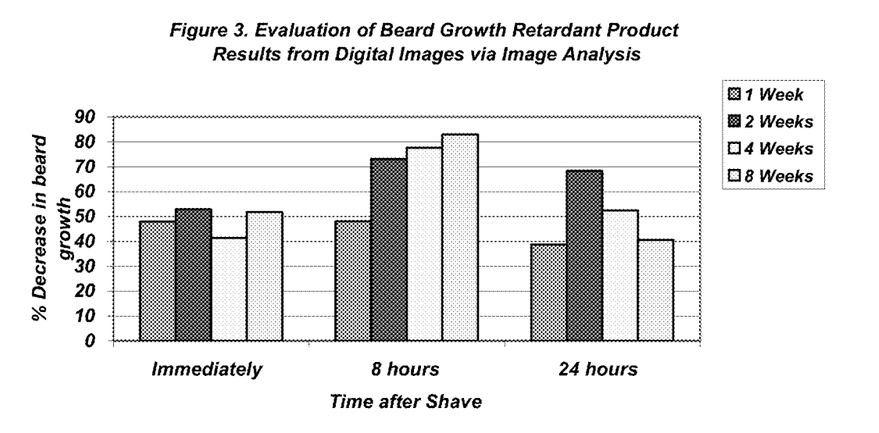
FIG. 3. Chart depicting results of image analysis of clinical study in Example 1 using inventive composition of the present invention.

Beard growth is evaluated via image analysis from close up digital photographs. These results show that the composition was very effective in reducing beard growth. Table 3 below and corresponding FIG. 3 summarize these results.

TABLE 3

Evaluation of Beard Growth Retardant Product
from Digital images via Image Analysis

| | % Decrease in beard growth | | | |
|---|---|---|---|---|
| Time after shaving | 1 Week | 2 Weeks | 4 Weeks | 8 Weeks |
| Immediately | 48.0 | 52.9 | 41.5 | 51.8 |
| 8 hours | 48.1 | 73.1 | 77.6 | 83.0 |
| 24 hours | 38.8 | 68.3 | 52.4 | 40.6 |

As seen from Table 3 above and corresponding FIG. 3, after one week and up to 8 weeks of treatment there is a 40-50% beard reduction immediately after shaving, thereby indicating a closer shave. The best results are seen 8 hours after shaving at the 5 O'clock shadow, where after one week of treatment there is a 48% reduction in beard growth and it steadily improves to 83% after 8 weeks. Twenty four hours after shaving there is a 38-68% reduction in beard growth after 1-8 weeks of treatment with some variation in the data.

Based on the results of the study in the above Example 1, it is seen that topical treatment with the composition is effective in improving beard texture, color and appearance and reducing beard growth.

EXAMPLE 2

Comparative Study

The following example provides a clinical study comparing an embodiment of the present invention with a conventional hair growth retardation product, using a control to note the differences.

Formation of Study Panel:

Adult women are recruited from a local population. The following criteria for inclusion and exclusion are based on the information obtained from the candidates and from an examination of the area that is involved in the study.

Inclusion Criteria:

To be considered as a potential subject, each candidate must:
 shaved legs daily;
 express willingness to cooperate with the investigator;
 convince the investigator that she was dependable and would comply with the study regimen;
 demonstrate the ability to understand the purpose of the study and what was required of her to bring the study to a meaningful conclusion;
 demonstrate the ability to understand the risks associated with participation; and
 demonstrate the ability to read and understand all the items in the informed consent document.

Exclusion Criteria:

A prospective participant is excluded if the interview or examination disclosed any of the following:
 a systemic illness that contra-indicates participation;
 any dermatological disorders in the areas that are to be used in the study;
 pregnant women or lactating mothers;
 using systemic or topical retinoids, antihistamines or similar agents.

Composition of Panel:

19 women who satisfy all the requirements itemized in the list of inclusion and exclusion criteria.

Test Products:

Product A: Inventive Composition (hereinafter "Hair Growth Retardation Complex")
 Soy Extract (0.2% Solgen 40)
 Phytospingosine 90.1%)
 Gorgonian Extract (0.5%)
 Yeast AE (1%)
 Ursolic Acid (0.2%)
 Glabridin (0.05%)

Product B: Conventional Hair Growth Retardation Product Sanguisorba Officinalis Root Extract
Product C: Traditional Moisturizer (Control)
Method of Application:

The women are instructed to apply the products to their legs three times a day, morning, afternoon, and evening, for 8 weeks. Group 1 applies product A to the right leg and product C to the left leg. Group 2 applies product B to the right leg and product C to the left leg. On the day of testing, the women do not apply the products for at least 12 hours before measurements were taken. Product use is monitored by a daily diary as well as assessment of remaining package content at the end of the study.

Clinical Test Procedure:

This is a double blinded study consisting of eight weeks of product use. The legs are the test site. The panelists refrain from using any treatment products on the test sites except for the test products provided. The panelists are instructed to shave their legs four days prior to each visit. Evaluations are carried out before product application (baseline), and at two, four, and eight weeks during the course of treatment. The panelists report to the Testing Center for testing.

Test Procedure:

1. Reduction of Hair Growth

At the outset of the study a particular area on the legs of each panelist demonstrating four days of hair growth is marked. The images of that specific portion of the leg are obtained using a fiber optic microscope (Hi-Scope, Vacaville, Calif.) at a magnification of 40× (approximately 1 sq. cm.) Ten sites are chosen per leg per panelist. The same area is photographed at each time point following the initial visit. The stored images are digitized and analyzed using an image analysis program, Optimas 6.51. The average hair length is calculated using total area 4 days after shaving at each time point to determine the amount of hair growth.

2. Results

TABLE 4

Comparative Study Results

| Time Point | Average | % Reduction | p-value |
|---|---|---|---|
| Hair Growth Retardation Product | | | |
| Baseline | 0.97 | | |
| 2 weeks | 0.83 | 14% | p > 0.05 |
| 4 weeks | 0.82 | 16% | p > 0.05 |
| 8 weeks | 0.69 | 29% | p < 0.05 |
| Conventional Hair Growth Retardation Product | | | |
| Baseline | 1.09 | | |
| 2 weeks | 0.94 | 14% | p > 0.05 |
| 4 weeks | 0.93 | 15% | p > 0.05 |
| 8 weeks | 0.88 | 20% | p < 0.05 |
| Control | | | |
| Baseline | 1.12 | | |
| 2 weeks | 1.12 | 0% | p > 0.05 |
| 4 weeks | 1.19 | −6% | p > 0.05 |
| 8 weeks | 1.12 | 0% | p > 0.05 |

Figure 4:
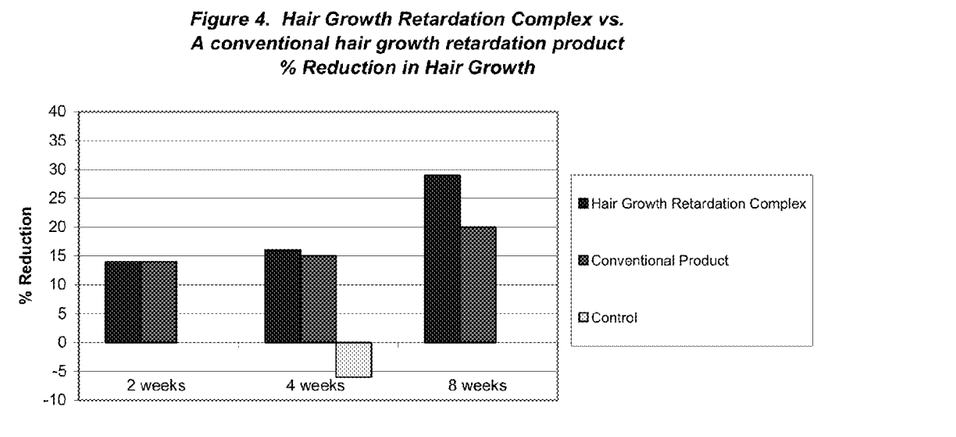
FIG. 4. Chart depicting results of comparative study between inventive composition and conventional hair growth retardation product.

As can be seen in Table 4 above and corresponding FIG. 4, the hair growth retardation product incorporating the inventive composition reduces hair growth by 29% after 8 weeks of use, as opposed to 20% reduction with the conventional hair growth retardation product and 0% using the control.

EXAMPLE 3

Comparative Study

The following example provides a clinical study comparing the inventive composition with the combination of ornithine decarboxylase inhibitor, anti-angiogenic active and an anti-inflammatory and the alternate embodiment including the 5 alpha reductase inhibitor in retarding hair growth.

Formation of Study Panel:

Adult men who were interested in taking part in this study were recruited from a local population. The following criteria for inclusion and exclusion were based on the information obtained from the candidates and from an examination of the area that was involved in the study.

Inclusion Criteria:

To be considered as a potential subject, each candidate must have:

a 5 o'clock shadow

Exclusion Criteria:

A prospective participant is excluded if the interview or examination disclosed any of the following:

a systemic illness that contra-indicates participation;

any dermatological disorders in the areas that were to be used in the study; or uses systemic or topical retinoids, antihistamines or similar agents.

Composition of Panel:

The panel is composed of 27 men who satisfy all the requirements itemized in the list of inclusion and exclusion criteria.

Test Products:

Group 1: Inventive composition with 0.1% 5 alpha reductase inhibitor, saw palmetto.

Group 2: Inventive composition without 5 alpha reductase inhibitor.

Method of Application:

Procedure for Shaving:

The panelists are instructed to report for all visits with a 24 hour beard growth. The men then shave with their own razor and shaving cream. Measurements are taken immediately after shaving, and after 8 and 24 hours.

The men are instructed to apply the product to their face two times a day, morning and evening, for 8 weeks. On the day of testing, the men do not apply the products for at least 12 hours before measurements were taken. Product use is monitored by a daily diary as well as assessment of remaining package content at the end of the study.

Clinical Test Procedure:

This is a double blinded controlled study consisting of eight weeks product use. The test site is the face. The men refrain from using any treatment products on the test sites except for the test products provided. The panelists are instructed to report to the testing center with at least a 24 hour beard growth. Evaluations are carried out before product application (baseline), and after four, and eight weeks during the course of treatment.

Test Procedure:

1. Reduction of Hair Growth

At the outset of the study a particular area on the face of each panelist is marked. The images of that specific portion of the face are obtained using a Fuji S-2 Digital Camera with a Canfield epilume adaptation. The Canfield Epilume allows for close up contact photos to be taken at a fixed distance. The same area is photographed immediately, 8 hours, and 24 hours after shaving at each visit. The stored images are digitized and analyzed using an image analysis program, Optimas 6.51.

Shave Time—

At each time point the men use an electronic timer to measure the length of time needed to shave.

Self Evaluations—

A self evaluation is performed by each panelist on the appearance of their beard, 8 and 24 hours after shaving. The following 10 point analog scale is used:

| 0 | 10 |
|---|---|
| Not Noticeable | Extremely Noticeable |

2. Results of Hair Retardation

TABLE 5

| | Hair Retardation | | Panelists Assessment of Beard Appearance | | Shave Time |
|---|---|---|---|---|---|
| | 8 hours | 24 hours | 8 hours | 24 hours | |
| Group 1 Inventive Composition with 5 alpha reductase inhibitor | | | | | |
| 4 weeks | 30% | 29% | 24% | 21% | 15% |
| 8 weeks | 47% | 39% | 30% | 27% | 20% |
| Group 2 Inventive Composition without 5 alpha reductase inhibitor | | | | | |
| 4 weeks | 17% | 27% | 19% | 15% | −6% |
| 8 weeks | 25% | 38% | 23% | 19% | 1% |

As can be seen in Tables 4 and 5 above, after eight weeks of product use with the composition containing the 5 alpha reductase inhibitor, panelists experienced a 47% reduction in hair growth eight hours after shaving, as compared to a 17% reduction without the addition of the 5 alpha reductase inhibitor in the product. Reduction in the appearance of hair growth was 30% with the 5 alpha reductase inhibitor in the product and 23% without, eight hours after shaving.

It should be understood that the specific forms of the invention herein illustrated and described are intended to be representative only. Changes, including but not limited to those suggested in this specification, may be made in the illustrated embodiments without departing from the clear teachings of the disclosure. Accordingly, reference should be made to the following appended claims in determining the full scope of the invention.

What is claimed is:

1. A method of retarding the growth of hair comprising:
   applying a topical composition, said topical composition comprising:
   a) from 0.1 to 50% of an ornithine decarboxylase inhibitor, said ornithine decarboxylase inhibitor being a pentacyclic triterprene;
   b) from 0.01 to 10% of an anti-angiogenic active agent;
   c) from 0.0001 to 20% of an anti-inflammatory; and
   d) a cosmetically acceptable vehicle.

2. The method of claim 1 wherein said pentacyclic triterpene is selected from the group consisting of ursolic acid, betulin, betulinic acid, oleanolic acid, betulin succinate, betulin di-succinate, betulin glutarate, and betulin di-glutarate.

3. The method of claim 1 wherein the anti-angiogenic active agent is a sphingo lipid selected from the group consisting of phytosphingosine, dihydrosphingosine, sphingosine and dehydrosphingosine.

4. The method of claim 1 wherein the anti-angiogenic active agent is selected from the group consisting of magnolia extract, shark cartilage, and tetrahydrocurcumin.

5. The method of claim 1 wherein the anti-inflammatory is selected from the group consisting of gorgonian extract, hoelen extract, ximenynic acid, hesperitin, tea polyphenols, and licorice extract.

6. The method of claim 1 wherein the composition further comprises a whitening agent selected from the group consisting of:
   a) yeast extract;
   b) ferulic acid;
   c) ascorbyl tetraisopalmitate;
   d) sodium hinokitol;
   e) glabridin;
   f) etioline;
   g) phytoclar II;
   h) arbutin;
   i) resveratrol; and
   j) kojic acid.

7. The method of claim 1 wherein the composition further comprises a plant extract selected from the group consisting of soy extract, wild yam and ginseng.

8. The method of claim 1 wherein the composition further comprises a 5 alpha reductase inhibitor selected from the group consisting of:
   a) saw palmetto;
   b) woodworm;
   c) liposome encapsulated azeleic acid;
   d) chouji liquid;
   e) zinc salt of L-pyrollidone carboxylic acid;
   f) a mixture comprising:
      (i) water;
      (ii) hydrolyzed soy protein,
      (iii) 3-aminopropane;
      (iv) sulfonic acid; and
      (v) sodium chondroitin sulfate;
   g) phlorogine;
   h) isolutrol;
   i) progesterone;
   j) (5,20-R)-4-diazo-21-hydroxy-20-methylpregnan-3-one;
   k) (4R)-5-10-seco-19-Norpregna-4,5-diene-3,10,20,tri-one;
   l) 4-androstene-3-one-17-carboxylic acid;
   m) methyl ester of 4-androstene-3-one-17-carboxylic acid;
   n) 17-beta-N,N-diethylcarbamoyl-9-methyl-4-aza-5-alpha-androstane-3-one-;
   o) 11-alphaOH-progesterone;
   p) 17-alpha-OH-progesterone; and
   q) 20-alpha-OH-progesterone.

9. A method of retarding hair growth comprising applying a cosmetic composition comprising:
   a) from 0.1 to 50% of a penticylic triterpene;
   b) from 0.01 to 10% of a sphingolipid;
   c) from 0.0001 to 20% of gorgonian extract; and
   d) a cosmetically acceptable vehicle.

10. The method of claim 9 wherein the pentacyclic triterpene is selected from the group consisting of ursolic acid, betulin, betulinic acid, oleanolic acid, betulin succinate, betulin di-succinate, betulin glutarate, and betulin di-glutarate and polyethylene glycol.

11. The method of claim 9 wherein the sphingo lipid is selected from the group consisting of phytosphingosine, dihydrosphingosine, sphingosine and dehydrosphingosine.

12. The method of claim 9 wherein the composition further comprises an anti-angiogenic active selected from the group consisting of magnolia extract, shark cartilage, and tetrahydrocurcumin.

13. The method of claim 9 wherein the composition further comprises a whitening agent selected from the group consisting of:
   a) yeast extract;
   b) ferulic acid;
   c) ascorbyl tetraisopalmitate;
   d) sodium hinokitol;
   e) glabridin;
   f) etioline;
   g) phytoclar II;
   h) arbutin;
   i) resveratrol; and
   j) kojic acid.

14. The method of claim 9 wherein the composition further comprises a plant extract selected from the group consisting of soy extract, wild yam, and ginseng.

15. The method of claim 9 wherein the composition further comprises a 5 alpha reductase inhibitor selected from the group consisting of:
   a) saw palmetto;
   b) woodworm;
   c) liposome encapsulated azeleic acid;
   d) chouji liquid;
   e) zinc salt of L-pyrollidone carboxylic acid;
   f) a mixture comprising:
      (i) water;
      (ii) hydrolyzed soy protein,
      (iii) 3-aminopropane;
      (iv) sulfonic acid; and
      (v) sodium chondroitin sulfate;
   g) phlorogine;
   h) isolutrol;
   i) progesterone;
   j) (5,20-R)-4-diazo-21-hydroxy-20-methylpregnan-3-one;
   k) (4R)-5-10-seco-19-Norpregna-4,5-diene-3,10,20,tri-one;
   l) 4-androstene-3-one-17-carboxylic acid;
   m) methyl ester of 4-androstene-3-one-17-carboxylic acid;
   n) 17-beta-N,N-diethylcarbamoyl-9-methyl-4-aza-5-alpha-androstane-3-one-;
   o) 11-alphaOH-progesterone;
   p) 17-alpha-OH-progesterone; and
   q) 20-alpha-OH-progesterone.

* * * * *